United States Patent [19]

Fukura et al.

[11] Patent Number: 5,161,538
[45] Date of Patent: Nov. 10, 1992

[54] BLOOD PRESSURE MEASURING DEVICE

[75] Inventors: Masashi Fukura, Kyoto; Yoshinori Miyawaki, Otsu, both of Japan

[73] Assignee: Omron Corporation, Kyoto, Japan

[21] Appl. No.: 743,067

[22] Filed: Aug. 9, 1991

[30] Foreign Application Priority Data

Aug. 9, 1990 [JP] Japan ................. 2-84592[U]

[51] Int. Cl.$^5$ .............................. A61B 5/022
[52] U.S. Cl. ....................... 128/677; 128/680
[58] Field of Search ............ 128/677, 630-633

[56] References Cited

U.S. PATENT DOCUMENTS

| | | | |
|---|---|---|---|
| 4,313,445 | 2/1982 | Georgi | 128/680 |
| 4,546,775 | 10/1985 | Medero | 128/680 |
| 4,872,461 | 10/1989 | Miyawaki | 128/681 |

FOREIGN PATENT DOCUMENTS 3612532 4/1986 Fed. Rep. of Germany.

Primary Examiner—Lee S. Cohen
Assistant Examiner—Robert L. Nasser
Attorney, Agent, or Firm—Fish & Richardson

[57] ABSTRACT

A blood pressure measuring device is provided which comprises a cuff for pressuring an artery, electronic circuitry made up of a clock, control unit, and blood pressure measuring unit for measuring blood pressure and controlling the device, and a cuff pressurizing and depressurizing unit. The basic components of the device are used to effectively give the patient, through a feeling of pressure from the cuff, information such as a signal indicating the start of measurement, by momentarily pressurizing the cuff then depressurizing it. This signal can be detected by hearing imparied patients as well as healthy patients who are in a noisy environment, but can not be noticed by others in close proximity to the patient.

2 Claims, 5 Drawing Sheets

BLOOD PRESSURE MEASURING DEVICE

FIELD OF THE INVENTION

This application is related to a blood pressure measuring device, and more specifically to the announcement of blood pressure measuring to the patient.

BACKGROUND OF THE INVENTION

A blood pressure meter is conventionally provided with a cuff pressuring an artery, a pressurizing means or pump to give pressure to the cuff, an air release means for depressurizing the cuff, and a blood pressure reading means. It is also necessary to inform the patient of the start of measurement, for this a buzzer is provided to sound immediately preceding the start of measurement.

FIG. 4 shows a flow chart of a conventional blood pressure meter. The patient, with the cuff in place around his upper arm pushes a start switch. It is then determined whether it is time for the blood pressure measurement to be taken (step 11). If the answer to step 11 is yes, the buzzer sounds (step 12) announcing to the patient that blood pressure measurement is about to begin. Thus the patient can assume a proper position for the measurement and remain still. At the start of the measurement, as shown in FIG. 5, both the slow release valve and the rapid release valve are closed, and the cuff is pressurized to a point higher than the Systolic blood pressure to block the flow of blood through an artery. Next the slow release valve is opened and as the pressure decreases the systolic and diastolic blood pressure values are measured by a blood pressure measuring unit (step 13). Upon completion of the blood pressure measurement the rapid release valve is opened to rapidly depressurize the cuff. Step 14 determines if the blood pressure is to be measured on a regular basis at given intervals of time, if the answer to step 14 is yes, the process described above is repeated.

In the conventional blood pressure measuring device the start, completion, or error of the measurement is announced by the sounding of a buzzer. A problem with this is that it does not enable the hearing impaired to realize that these events are taking place. Even healthy patients may have difficulties hearing the sounding of the buzzer due to noise in the environment. When the patient cannot hear the buzzer, measurement will seem to start suddenly without any indication to the patient. In other words there is a sudden feeling of pressure, which may cause movement of the patient due to the surprise of feeling the unannounced pressure. This movement may adversely affect the accuracy of the measurement. Further, with the use of a buzzer to announce the start of measurement, people around the patient are notified that the patient will have his blood pressure measured. This may cause undue nervousness or anxiety in the patient and in turn affect the accuracy of the measurement.

SUMMARY OF THE INVENTION

It is one objective of this invention to solve the above mentioned problems, and more specifically to clearly announce the start of measurement and other information to only the patient who is being measured.

It is another object of this invention to provide a blood pressure meter which can measure the blood pressure of a patient who is in a relaxed and prepared mental condition.

It is further an object of this invention to accomplish the above using the basic components of a conventional blood pressure measuring device.

According to this invention there is provided a blood pressure measuring device comprising a cuff for pressuring an artery, a pressure increasing unit for pressurizing the cuff, a releasing unit for depressurizing the cuff, a blood pressure measuring unit for taking actual measurements, and a control unit for controlling the above functions; wherein the pressurizing unit is driven by the control unit to inform the patient of certain information, such as the start of measurement, regarding the blood pressure measuring process by causing a small increase and decrease in the pressure of the cuff. Thus a blood pressure measuring device is provided which indicates the start of measurement by a brief pressurizing, 50 mmHg for example, and depressurizing of the cuff. This conveys a feeling of slight pressure to the patient for any desired number of times. Accordingly, not only can the hearing impaired patient recognize the signal, but a healthy patient in a noisy environment will have no trouble detecting the signal. Additionally, the patient can be informed of the impending measurement without giving notice to others around him. This provides for a more relaxed mental state, and reduces inaccurate blood pressure measurements which may be caused by nervousness or anxiety.

Furthermore this invention makes use of the originally provided components of a blood pressure measuring device to indicate the start or other information. Thus there is no need to provide an extra announcement unit, such as the buzzer of the related art.

BRIEF DESCRIPTION OF THE DRAWINGS

The above and other objects, advantages and features of this invention will be more fully understood from the following detailed description provided in conjunction with the following figures, of which.

DETAILED DESCRIPTION OF THE PREFERRED EMBODIMENT

Figure 3:
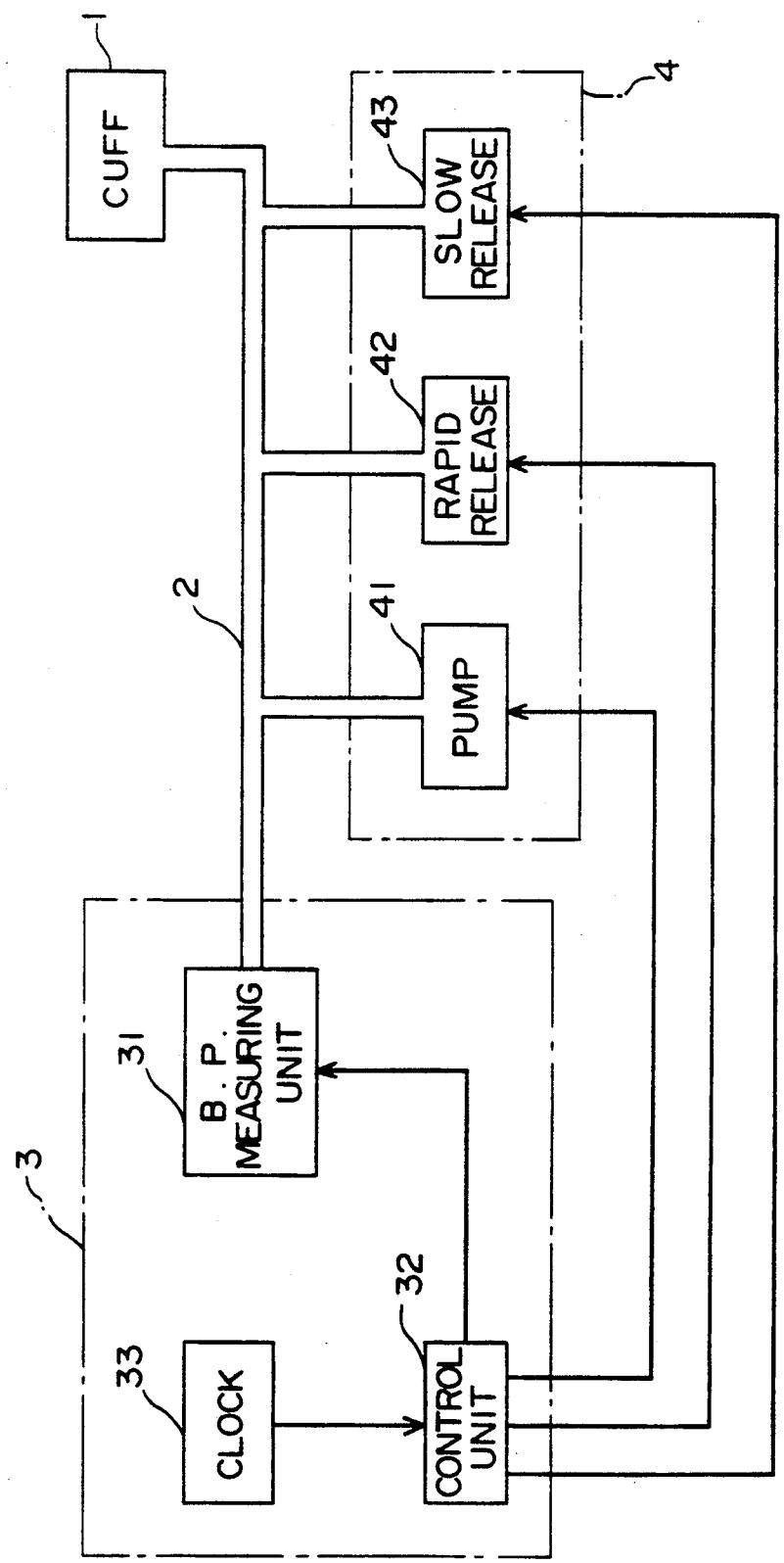
FIG. 3 shows a block diagram of the circuitry of this invention.
Figure 4:
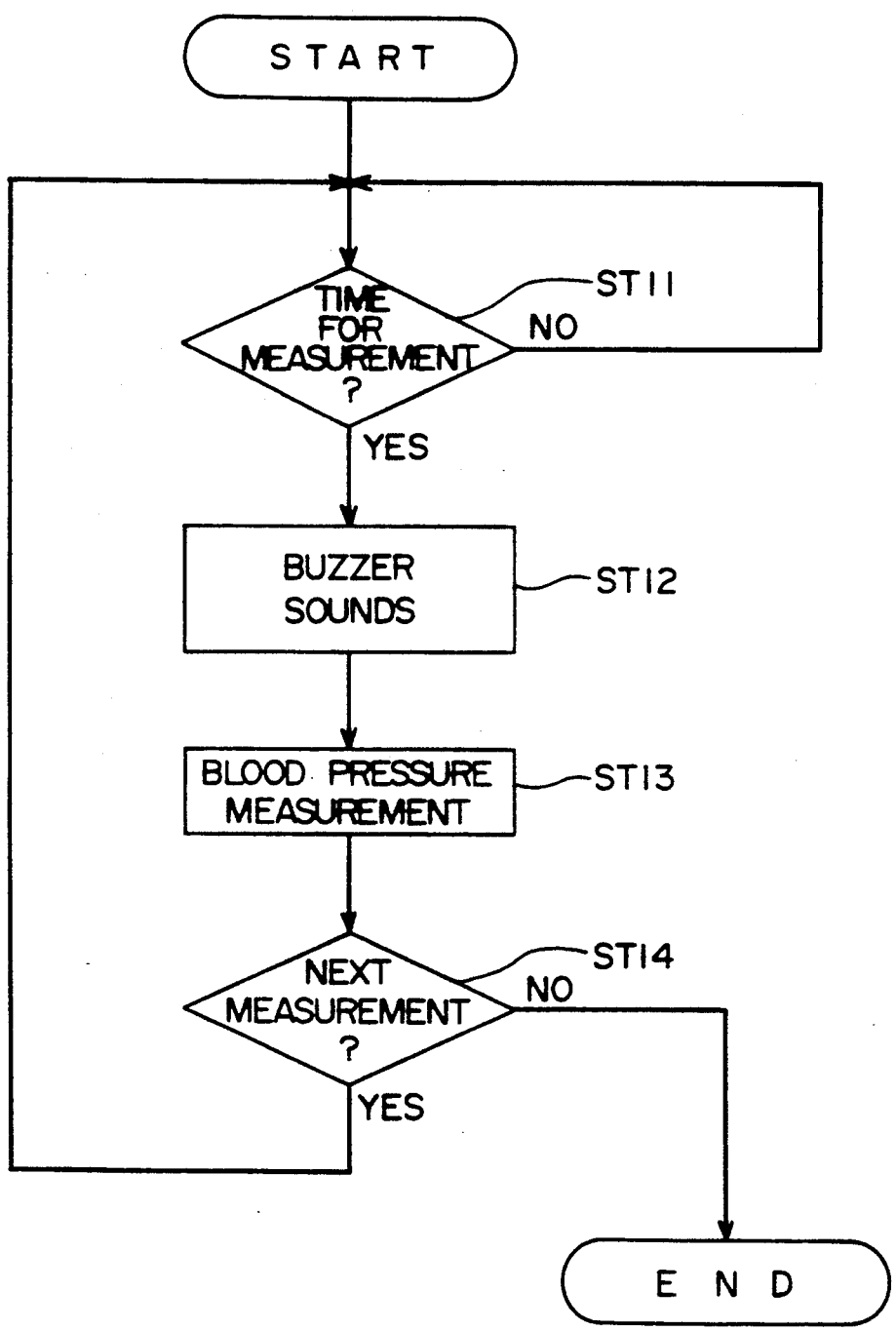
FIG. 4 is a flow chart of the operation of a conventional blood pressure measuring device.
Figure 5:
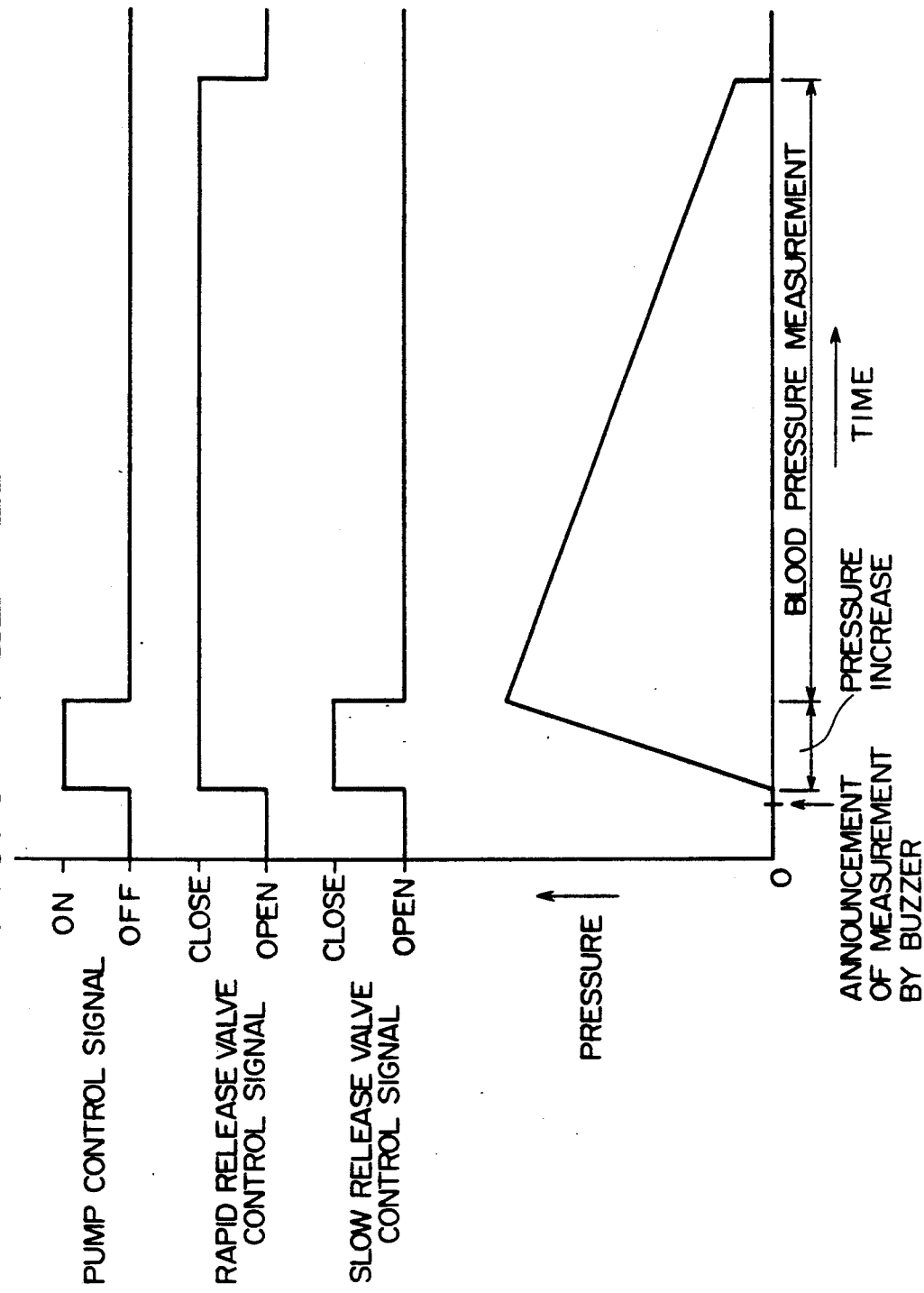
FIG. 5 shows a graph of the changes in cuff pressure and the buzzer sound, and a time chart for the operation of the pressurizing pump and release valves of a conventional blood pressure measuring device.

FIG. 3 shows a block diagram of the blood pressure measuring device of this invention which includes a cuff 1 for pressuring an artery, electronic circuitry 3 connected to the cuff 1 through air tube 2 for taking blood pressure measurements and controlling the overall functions of the device, and a cuff pressurizing and depressurizing unit 4 connected to the cuff 1 through air tube 2 for controlling the pressure in the cuff. The cuff pressurizing and depressurizing unit 4 includes a pressurizing pump 41 which is used to pressurize the cuff 1, a rapid release valve 42 for rapidly depressurizing the cuff 1, and slow release valve 43 for slowly depressurizing the cuff 1 while blood pressure measurement is taking place. The electronic circuitry 3 includes a blood pressure measuring unit 31, a control unit 32, and a clock 33. Control unit 32 is electrically connected to pressurizing pump 41, rapid release valve 42, and slow release valve 43. The control unit 32 drives the pressurizing pump 41, and blood pressure measuring unit 31, and controls the opening and closing of rapid release valve 42 and slow release valve 43 based on a signal from the clock 33.

Figure 2:
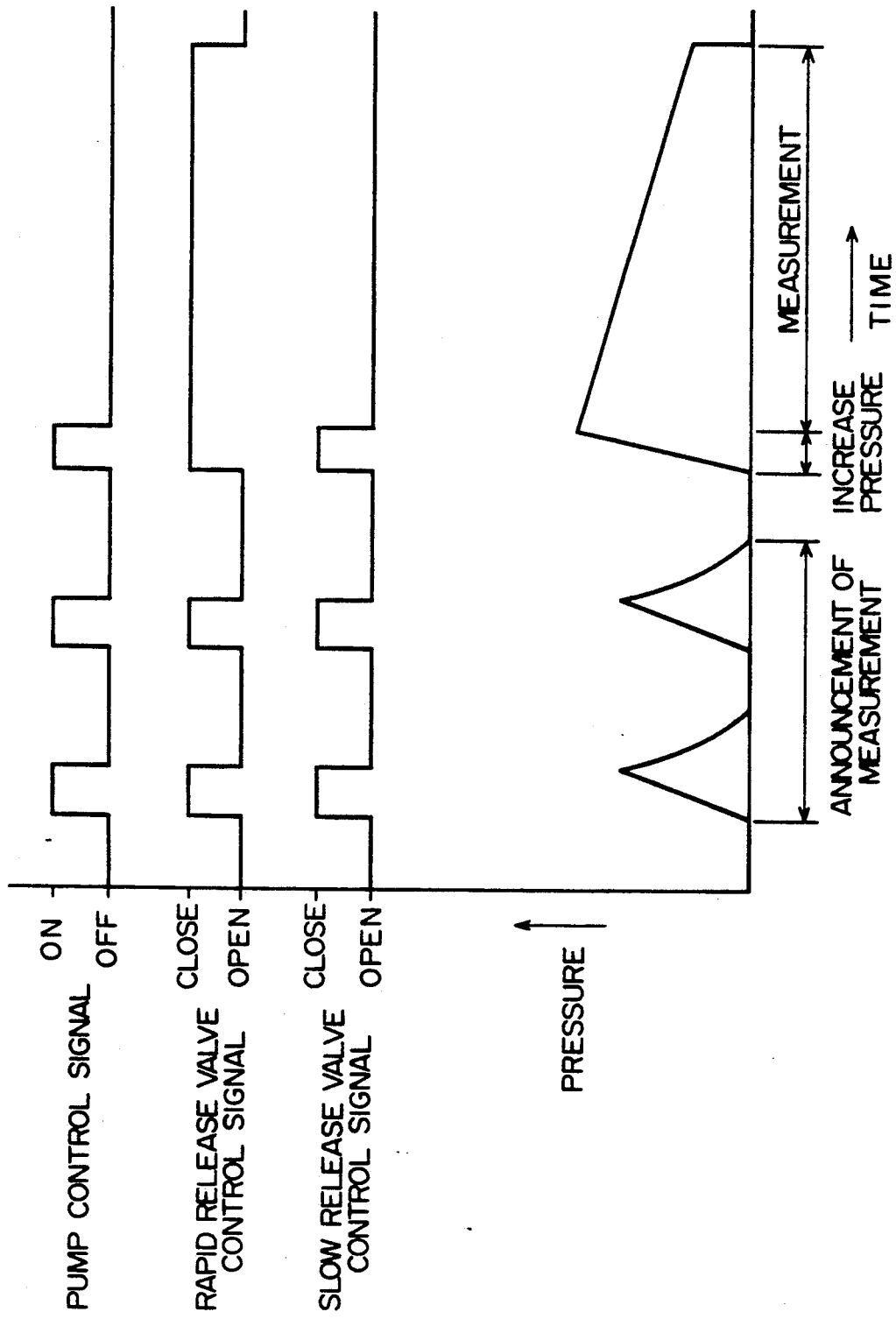
FIG. 2 shows a graph of the changes in cuff pressure, and a time chart for the operation of the pressurizing pump, the slow release valve, and rapid release valve of this invention.

The major point of this embodiment is to announce the start of blood pressure measurement by applying a short interval of pressurizing and depressurizing to cuff 1 before the control unit 32 initiates the start of blood pressure measurement. As shown in FIG. 2, while rapid release valve 42 and slow release valve 43 are closed, the pressurizing pump 31 is driven for a short time to slightly pressurize the cuff 1, 50 mmHg for instance. Then the rapid and slow release valves 42 and 43 are opened immediately and the cuff is depressurized, so that there is only a short interval of pressure felt by the patient to announce the start of measurement. Following this the blood pressure measurement takes place.

At the start of the measurement, shown in FIG. 2, slow release valve 43 and rapid release valve 42 are in a closed state, and the pressurizing pump 41 is driven to pressurize the cuff 1. After pressurizing the cuff to the predetermined value, the slow release stage is begun by opening only the slow release valve 43. Under this slow release stage the blood pressure measuring unit 31 measures the systolic and diastolic blood pressures. Finally upon the completion of the measurement, the rapid release valve 42 is opened to rapidly depressurize the cuff.

Figure 1:
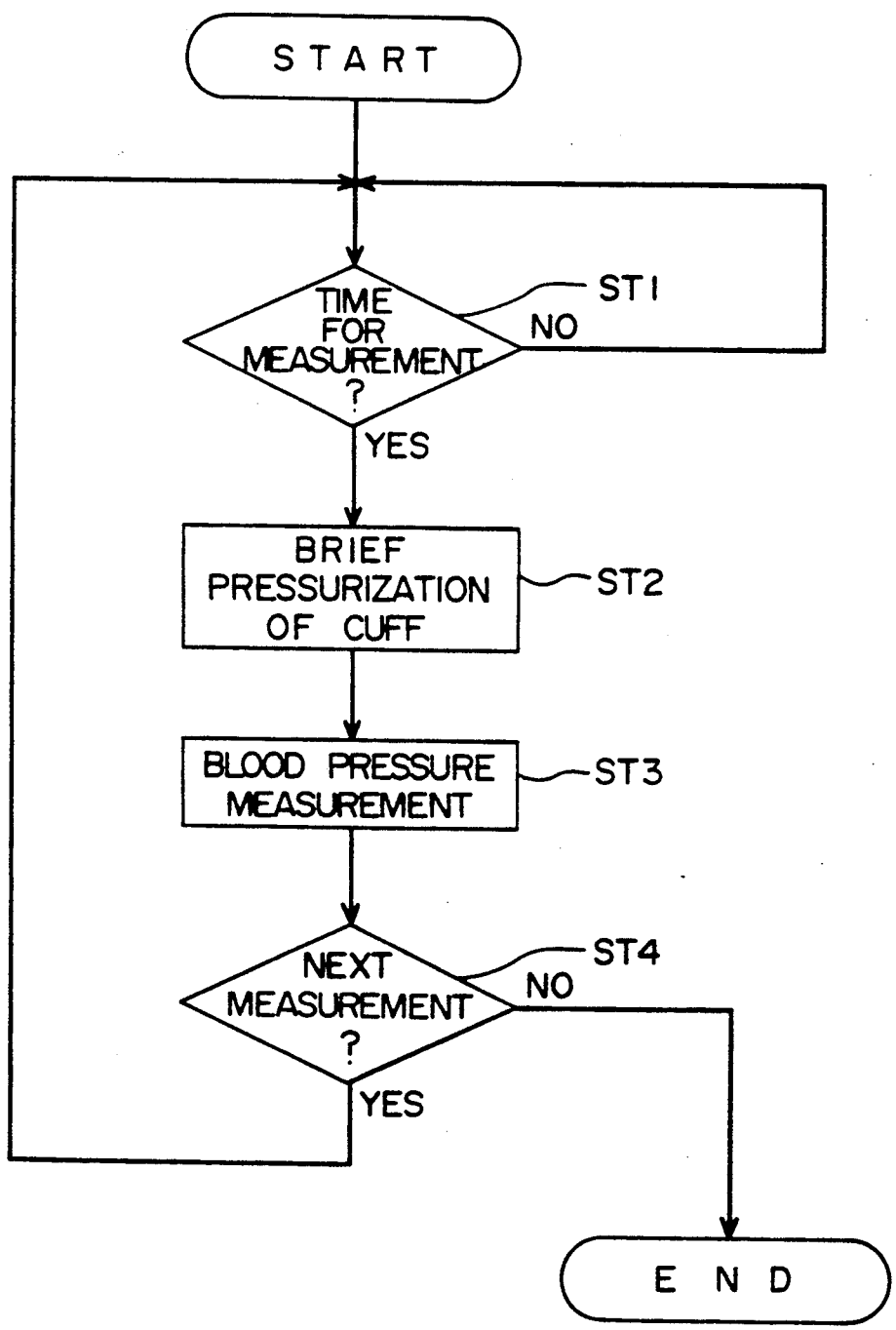
FIG. 1 is a flow chart displaying the operation of the blood pressure measuring device of this invention.

FIG. 1 shows a flow chart of the operation of the blood pressure measuring device of this invention. In step 1 it is determined whether it is time to measure the blood pressure. More specifically, it is determined if the cuff 1 is in the blood pressure measuring state, a state of non-pressurization for example, after the start button has been pushed. If the answer to step 1 is yes then the start of blood pressure measuring is announced by pressurizing the cuff for a number of brief intervals (step 2). As illustrated in FIGS. 2 and 3, the control unit 32 sends a signal to the pump 41, rapid release valve and slow release valve respectively. Release valves 42 and 43 are closed and the pump 41 is driven to pressurize the cuff 1 to some 50 mmHg, the pump 41 is then immediately stopped and the slow and rapid release valves 42 and 43 are opened, thereby depressurizing the cuff 1 back to the non-pressurized state. As a result of this the upper arm wound by the cuff 1 is applied a slight feeling of pressure for a number of brief intervals of time, thereby indicating to the patient that measurement will begin. In this embodiment the announcement of the start is made twice, upon recognition of the start signal the patient takes a position suitable for blood pressure measurement. For instance taking a relaxed position controlling the movement of the body. In this way the blood pressure measurement will be taken on a patient who is in a relaxed physical and mental state. The blood pressure measurement is then carried out (step 3). As shown in FIG. 2, first the slow release valve 43 and rapid release valve 42 are closed and pump 41 is driven to pressurize the cuff 1 to a point higher than the systolic pressure, after this the slow release valve 43 is opened and the systolic and diastolic blood pressure is measured during this slow release stage. Upon completion of the blood pressure measurement the rapid release valve 42 is opened to rapidly depressurize the cuff 1. In step 4 it is determined if a next measurement is necessary. When continuous measurement is desired, the answer to this is yes and the process of blood pressure measurement is repeated in the same manner. Thus in this embodiment of a blood pressure measuring device, the patient is notified of the start of measurement by the pressurization and depressurization of the cuff 1, accordingly the notice is not made by a buzzer in the conventional manner. Not only can the hearing impaired recognize the signal but a healthy person can also recognize the signal under noisy conditions. Still further, the announcement of the start of measurement by using the feeling of pressure can discreetly indicate to the patient the start of measurement, thereby not informing the others around him and causing a feeling of nervousness and an inaccurate measurement. Yet further the announcement is made by using the pre-existing components of the device which make the use of extra announcement devices, such as a buzzer, unnecessary, thereby reducing cost.

In the above embodiment the cuff is wound around the upper arm, it should also be made clear that this invention can be applied to the finger or other type blood pressure measuring devices as well. Additionally the information indicated by the feeling of pressure is not limited to the start of measurement, it can be used to indicate other information such as the normal completion, measurement error, or run down battery. Any such concept can be applied to the ideas of this invention. Further the above description and the accompanying drawings are merely illustrative of the application of the principles of the present invention and are not limiting. Numerous other arrangements which fall within the spirit and scope of the invention may be readily devised by those skilled in the art. Accordingly, the invention is not limited by the foregoing description, but is only limited by the scope of the appended claims.

What we claim is:

1. A blood pressure measuring device comprising:
    cuff means for applying pressure to an artery of a patient,
    pressurizing means for pressurizing said cuff means,
    depressurizing means for depressurizing said cuff means,
    blood pressure measuring means for determining systolic and diastolic blood pressure, and
    control means for controlling said pressurizing means, said depressurizing means, and said blood pressure measuring means such that the patient is given notice that a blood pressure measurement is about to begin by a brief pressurization and depressurization of said cuff means.

2. The blood pressure measuring device of claim 1, wherein during the brief pressurization and depressurization the cuff means is pressurized by the pressurizing means to a pressure of 50 mmHg.

* * * * *